United States Patent
Homman et al.

(10) Patent No.: US 9,119,852 B2
(45) Date of Patent: Sep. 1, 2015

(54) PHARMACEUTICAL FORMULATION FOR TREATING HERPES VIRUS INFECTION COMPRISING 2,3-DIMETHYL-6-(N,N-DIMETHYL-AMINOETHYL)-6H-INDOLO-(2,3-B) QUINOXALINE

(76) Inventors: Mohammed Homman, Nacka (SE); Jan Bergman, Spanga (SE)

( * ) Notice: Subject to any disclaimer, the term of this patent is extended or adjusted under 35 U.S.C. 154(b) by 0 days.

(21) Appl. No.: 13/984,105

(22) PCT Filed: Feb. 17, 2012

(86) PCT No.: PCT/EP2012/052763
§ 371 (c)(1),
(2), (4) Date: Aug. 7, 2013

(87) PCT Pub. No.: WO2012/110631
PCT Pub. Date: Aug. 23, 2012

(65) Prior Publication Data
US 2013/0310392 A1    Nov. 21, 2013

Related U.S. Application Data

(60) Provisional application No. 61/444,275, filed on Feb. 18, 2011.

(30) Foreign Application Priority Data

Feb. 18, 2011  (EP) ...................... 11154979

(51) Int. Cl.
*A61K 31/4985* (2006.01)
*C07D 241/38* (2006.01)
*A61K 9/00* (2006.01)
*A61K 9/06* (2006.01)
*A61K 45/06* (2006.01)

(52) U.S. Cl.
CPC ........... *A61K 31/4985* (2013.01); *A61K 9/0014* (2013.01); *A61K 9/06* (2013.01); *A61K 45/06* (2013.01)

(58) Field of Classification Search
CPC .......................... A61K 31/4985; C07D 241/38
USPC .......................... 514/250; 544/343
See application file for complete search history.

(56) References Cited

FOREIGN PATENT DOCUMENTS

| WO | 87/04436 A1 | 7/1987 |
| WO | 96/24355 A1 | 8/1996 |
| WO | 2007/084073 A1 | 7/2007 |

OTHER PUBLICATIONS

Harmenberg, et al. Antimicrobial Agents and Chemotherapy, 32(11), 1988, 1720-1724.*
Chan-Tack, et al. Combined Clinical and Biostatistics Review, 2009, 1-74.*
Skarin Tobias et al.:"Protection against 12-O-tetradecanoylphorbol-13-acetate induced skin-hyperplasia and tumor promotion, in a two-stage carcinogenesis mouse model, by the 2,3-dimethyl-6(2-dimethylaminoethyl)-6H-indolo-(2,3-b)quinoxaline analogue of ellipticine", Chemico-Biological Interactions, vol. 122, No. 2, Sep. 30, 1999, pp. 89-106, XP002630891, ISSN: 0009-2797 abstract p. 92, paragraph 2. 3; figure 2, tables 1,2.
Harmenberg J et al.: "The mechanism of action of the anti-herpes virus compound 2,3-dimethyl-6(2-dimethylaminoethyl)-6H-indolo-(2,3-b)quinoxaline", Antiviral Research, Elsevier BV, NL, vol. 15, No. 3, Mar. 1, 1991, pp. 193-204, XP023702771, ISSN: 0166-3542, DOI:10.1016/0166-3542(91)90066-Z [retrieved on Mar. 1, 1991] the whole document.
Spruance S L et al.: "Treatment of Herpes Simplex Labialis", Herpes, Cambridge Medical Publications, Worthing, GB, vol. 9, No. 3, Jan. 1, 2002, pp. 64-69, XP009070057, ISSN: 0969-7667 the whole document.
Kleymann G: "Novel agents and strategies to treat herpes simplex virus infections", Expert Opinion on Investigational Drugs 20030201 GB LNKDDOI: 10.1517/13543784.12.2.165, vol. 12, No. 2, Feb. 1, 2003, pp. 165-183, XP002630892, ISSN: 1354-3784 the whole document.
International Search Report, dated Mar. 14, 2012, from corresponding PCT application.

* cited by examiner

*Primary Examiner* — Douglas M Willis
(74) *Attorney, Agent, or Firm* — Young & Thompson

(57) ABSTRACT

A pharmaceutical composition for topical administration including 2,3-dimethyl-6-(N,N-dimethylaminoethyl)-6H-indolo-(2,3-b)quinoxaline (B-220) or a pharmaceutically acceptable salt thereof in a pharmaceutically acceptable carrier. The composition is useful for the treatment of herpes virus infections of the skin or mucous membranes in a mammal subject.

9 Claims, No Drawings

PHARMACEUTICAL FORMULATION FOR TREATING HERPES VIRUS INFECTION COMPRISING 2,3-DIMETHYL-6-(N,N-DIMETHYLAMINO-ETHYL)-6H-INDOLO-(2,3-B) QUINOXALINE

FIELD OF THE INVENTION

The present invention relates to a pharmaceutical composition for topical administration suitable for the prophylaxis and treatment of herpes virus infections. The pharmaceutical composition comprises the compound 2,3-dimethyl-6-(N,N-dimethylaminoethyl)-6H-indolo-(2,3-b)quinoxaline (herein below also referred to as B-220) or a pharmaceutically acceptable salt thereof, optionally in combination with at least one additional therapeutically active, ingredient suitable for topical administration, e.g. selected from antiviral agents, antibiotics, analgesics, anaesthetic agents, antiphlogistic agents, and anti-inflammatory agents.

BACKGROUND OF THE INVENTION

Herpes virus infections in humans can be caused by different human and animal herpes viruses, the most common being herpes simplex virus and varicella-zoster virus.

Following a primary infection with herpes simplex or varicella-zoster virus, the virus establishes latency in the sensory nerve cells for the rest of the patient's life and subsequently repeated virus reactivation can occur. Following a reactivation in the nerve cell the virus is transported through the nerves to the skin and then a lesion will develop. Immediately upon an outbreak of virus replication inflammation will follow. The inflammation contributes to the symptoms associated with herpes virus recurrence, including redness, swelling, itching and pain as well as lesions.

Herpes simplex viruses may be grouped into two serotypes, HSV type 1 (HSV-1) and type 2 (HSV-2), the clinical manifestations of which range from benign self-limiting orofacial and genital infections to potentially life threatening conditions such as encephalitis and generalized neonatal infections. Oral-facial HSV infections are primarily caused by HSV-1, which becomes latent after a primary infection e.g. in childhood. After reactivation a recurrent oral-facial HSV infection develops, more commonly known as a cold sore. About half of the patients experience early symptoms, e.g. pain, burning or itching at the site of the subsequent lesions. The condition is generally rapidly self-limiting and the healing time of a typical episode is about 10 days from the initial symptoms. Viral replication in the lip is initiated early and maximum virus load is attained 24 hours after the onset of the reactivation. The virus concentration is then dramatically reduced and typically virus cannot be isolated 70-80 hours after the onset.

The clinical presentation of genital HSV infections is similar to the oral-facial infections with some important exceptions. Genital HSV infections are most often caused by HSV-2 and following the primary infection the virus will latently infect sensory or autonomic ganglions. Reactivation will produce the local recurrent lesions on or near the genitals that are characteristic of the herpes infection.

A primary infection with varicella-zoster virus (VZV) causes chicken-pox. Like HSV, VZV becomes latent following the primary infection and can be activated as herpes zoster later on in life. Zoster usually results in skin rash and intensive acute pain. In 30% of the patients, the pain can be prolonged and continue for weeks or months after the rash has cleared up, or may even be permanent.

HSV and VZV may, in addition to mucous or cutaneous manifestations, also cause keratitis in the eyes. This condition is also recurrent and may cause blindness.

There are a number of antiviral agents which are active against the human herpes viruses. However, so far clinical success in the treatment of recurrent herpes virus infections has been only limited and there still exists no cure for herpes.

Various antivirals are used with varying success, e.g.: acyclovir (aciclovir), valacyclovir (valacyclovir), famciclovir, and penciclovir. For example, a cream formulation of acyclovir for topical application is sold by Ranbaxy under the generic name Zovirax.

WO96/024355 describes a combination formulation for topical administration comprising a topically acceptable antiviral agent, e.g. acyclovir, and an antiinflammatory glucocorticoid, e.g. hydrocortisone. A composition within the scope of said patent application, useful for the topical treatment of recurrent herpes labialis (cold sores) is commercially available as Xerclear™ (Xerese™ in the USA). Said composition contains 5% acyclovir and 1% hydrocortisone in a cream formulation.

There however still remains a need for effective drugs and methods of treatment for primary as well as recurrent herpes infections.

B-220 was disclosed for the first time in the PCT application published as WO87/04436, which showed the antiviral effect of a number of indoloquinoxalines against herpes simplex virus of both type 1 and 2. The antiviral effect was shown by injecting the test substance in mice receiving also an intracerebral injection of the virus.

The antiviral activity of B-220 against human cytomegalovirus has also been mentioned in the PCT application published as WO07/084073, where B-220 is used as a reference compound in a modified plaque assay.

SUMMARY OF THE INVENTION

It has now been found that primary and recurrent herpes virus infections can be surprisingly effectively treated by topical administration of B-220.

The invention therefore relates to a pharmaceutical composition for topical administration comprising 2,3-dimethyl-6-(N,N-dimethylaminoethyl)-6H-indolo-(2,3-b)quinoxaline (B-220) or a pharmaceutically acceptable salt thereof in a pharmaceutically acceptable carrier.

The composition of the invention is useful for topical administration to a mammal subject suffering from a primary or recurrent herpes virus infection, especially of oral-facial type.

In one embodiment, the pharmaceutical composition of the invention additionally comprises at least one additional therapeutically active ingredient suitable for topical administration.

According to one aspect, the invention relates to B-220 or a pharmaceutically acceptable salt thereof for use in the treatment of herpes virus infections of the skin or mucous membranes in a mammal subject by topical administration of a therapeutically effective dose thereof to the skin and/or mucous membrane of the mammal subject.

In one embodiment, the invention relates to B-220 or a pharmaceutically acceptable salt thereof is used in combination with at least one additional pharmaceutically active ingredient suitable for topical administration.

According to another aspect, the invention relates to a method of prophylactic and/or curative treatment of herpes virus infections of the skin or mucous membranes in a mammal subject comprising topical administration of a therapeutically effective dose of B-220 or a pharmaceutically acceptable salt thereof.

In one embodiment, the method also comprises topical administration, in combination or in sequence, of at least one additional pharmaceutically active ingredient suitable for topical administration, e.g. selected from antiviral agents, antibiotics, anaesthetic agents, analgesic agents, antiphlogistic agents, and anti-inflammatory agents.

DETAILED DESCRIPTION OF THE INVENTION

B-220, i.e. 2,3-dimethyl-6-(N,N-dimethylaminoethyl)-6H-indolo-(2,3-b)quinoxaline, has the structural formula

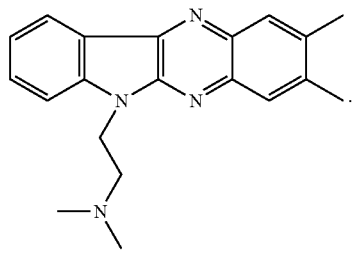 [SMILES: Cc1cc2nc3c4ccccc4n(CCN(C)C)c3nc2cc1C]

and may be prepared e.g. as described in WO87/04436, the contents of which is incorporated herein by reference.

Pharmaceutically acceptable salts of B-220 may be formed using any organic or inorganic, pharmaceutically acceptable acid, such as are well-known to the person of ordinary skill in the art. Pharmaceutically acceptable acid addition salts according to the invention are salts that are safe and effective for topical use in mammals and that possess the desired biological activity, e.g. hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, or p-toluenesulfonate salts.

The pharmaceutical composition of the invention comprises B-220 and at least one pharmaceutically acceptable excipient. In one embodiment of the invention, the pharmaceutical composition comprises B-220 or a pharmaceutically acceptable salt thereof in a pharmaceutical carrier suitable for topical delivery of the active ingredient.

In one embodiment, the pharmaceutical composition comprises B-220 or a pharmaceutically acceptable salt thereof and an additional therapeutically active ingredient, suitable for topical administration, e.g. selected from antiviral agents, antibiotics, anaesthetic agents, analgesic agents, antiphlogistic agents and anti-inflammatory agents.

In one embodiment, the additional therapeutically active ingredient comprises or is an antiviral agent. The antiviral agents suitable for the purposes of the present invention are topically acceptable antiviral compounds, which in addition to being specific inhibitors of herpes virus multiplication also are active after topical administration and in addition are pharmaceutically acceptable for topical administration. This means that the toxicity of the antivirals must be sufficiently low to allow for a continuous contact with the human body and in particular with the skin and mucous membranes. Examples of antiviral agents are substances within the group comprising compounds acting on viral DNA polymerase, such as nucleoside analogues after phosphorylation to their triphosphate forms; phosphonoformic and phosphonoacetic acids and their analogues; and other antiviral compounds having a different mechanism of action. As examples of antiviral agents which can be used in the combination of the invention can be mentioned acyclovir (ACV), ACV-phosphonate, brivudine (bromovinyldeoxyuridine, BVDU), carbocyclic BVDU, buciclovir, CDG (carbocyclic 2'-deoxyguanosine), cidofovir (HPMPC, GS504), cyclic HPMPC, desciclovir, edoxudine, famciclovir, ganciclovir (GCV), GCV-phosphonate, genivir (DIP-253), H2G (9-[4-hydroxy-2-(hydroxy-methyl)butyl]-guanine), HPMPA, lobucavir (bishydroxymethylcyclobutylguanine, BHCG), netivudine (zonavir, B W882C87), penciclovir, PMEA (9-(2-phosphonylmethoxy-ethyl)adenine), PMEDAP, sorivudine (brovavir, BV-araU), valacyclovir, 2242 (2-amino-7-(1,3-dihydroxy-2-propoxymethyl)purine), HOE 602, HOE 961; BPFA (batyl-PFA), PAA (phosphonoacetate), PFA (phosphonoformate); arildone, amantadine, BILD 1263, civamide (capsaicin), CRT, ISIS 2922, peptide T, tromantadine, virend, 1-docosanol (lidakol) and 348U87 (2-acetylpyridine-5-[2-chloro-anihno-thiocarbonyl]-thiocarbono-hydrazone).

Preferred antiviral agents are those with specific antiviral activity such as herpes specific nucleoside analogues which are preferentially phosphorylated in virus-infected cells and have very low or non-existent incorporation into cellular DNA as well as other compounds with specific antiviral activity. Acyclovir, for instance, has a selectivity ratio for the inhibitory activity against HSV-1 in vitro of about 2000. Among said preferred substances can in addition to acyclovir be mentioned brivudine, cidofovir, desciclovir, famciclovir, ganciclovir, HOE 961, lobucavir, netivudine, penciclovir, PMEA, sorivudine, valacyclovir, 2242, BPFA, PFA, PAA.

A suitable antiphlogistic agent, i.e. an agent capable of reducing inflammation, pain and/or fever, e.g. may be a nonsteroidal anti-inflammatory drug (NSAID), such as diclofenac (IUPAC name 2-(2,6-dichloranilino)phenylacetic acid), or ibuprofen, (IUPAC name (RS)-2-(4-(2-methylpropyl)phenyl)propanoic acid), or a pharmaceutically acceptable salt thereof, e.g. a sodium, potassium or diethylamine salt thereof.

A suitable anaesthetic agent e.g. may be lidocaine (IUPAC name 2-(diethylamino)-N-(2,6-dimethylphenyl)acetamide).

A suitable antiinflammatory agent e.g. may be adenosine (IUPAC name: (2R,3R,4S,5R)-2-(6-amino-9H-purin-9-yl)-5-(hydroxymethyl)oxolane-3,4-diol.

The antiinflammatory agent also may be selected from antiinflammatory glucocorticoids. A suitable glucocorticoid can be either naturally occurring or synthetic and can be selected from any of the Group I-ID glucocorticoids, according to a classification system for topical glucocorticoids used in the Nordic countries, corresponding to less potent, low or moderately potent glucocorticoids. Examples of glucocorticosteroids are alclometasone, amicinonide, beclomethasone, betamethasone, budesonide, ciclesonide, clobetasone, clocortolone, cloprednol, cortison, desonide, desoximethasone, dexamethasone, diflorosane, diflucortolone, difluprednate, fludrocortisone, fludroxycortid, flumethasone, flunisolide, fluocinolone acetonide, fluocinonide, fluocortin, fluocortolone, fluprednidene, fluticasone, halcinonide, halobetasol, halometasone, hydrocortisone, methylprednisolone, mometasone, paramethasone, prednisolone, prednicarbate, prednisone, prednylidene, rofleponide, tipredane and triamcinolone and their esters, salts and solvates, that is hydrates, where applicable.

Some preferred glucocorticoids are hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide; in particular hydrocortisone, budesonide and fluticasone.

A suitable antibiotic e.g. may be selected from clindomycin, erythromycin, mupirocin, bacitracin, polymyxin and neomycin.

The carrier of the pharmaceutical composition should be stable and pharmaceutically acceptable and suitable for topical application. It should also enable incorporation of sufficient amounts of B-220 or of the pharmaceutically acceptable salt thereof, and optionally additional active ingredient(s). In addition to conventional ingredients in creams, lotions, gels or ointments, aerosolizable liquids, and foams, compositions based on phospholipids, including sphingolipids can be advantageous. In a cream or ointment formulation the carrier may be white petrolatum.

A liquid carrier may include water, alcohols or glycols or water-alcohol/glycol blends, in which effective amounts of the active ingredient(s) according to the invention can be dissolved or dispersed, optionally with the aid of non-toxic surfactants. Adjuvants such as fragrances and antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, creams etc., for application directly to the skin and/or mucous membrane of the user.

A pharmaceutical composition of the invention can be used for the prophylaxis and/or treatment of herpes virus infections in mammals including man. In a preferred embodiment the composition is used for the treatment of primary or recurrent herpes virus infections. The treatment of infection should take place during the virus replication, preferably from the first appearance of redness/lesion or prodromal symptoms and for a period of 3-4 days at least. The formulation may be repeatedly applied, e.g. up to every two hours, during the whole episode until healing.

Prophylactic treatment may be performed in patients having regularly recurrent disease. In this case the formulation is applied to the area where a recurrence is expected before the appearance of the first symptoms. The compositions of the invention can be used to treat all types of herpes virus that replicate in the skin or the mucous membrane, e.g. HSV-1, HSV-2 and VZV.

The pharmaceutical compositions for topical administration according to the present invention are preferably creams, lotions, gels, sprays, foams, ointments or drops. The pharmaceutical compositions can be incorporated into plasters or patches to be applied to the skin of a patient to be treated for herpes infections or into pens or sticks for application to the skin or mucous membranes.

Liquid compositions can be applied from absorbent pads, used to impregnate bandages and other dressings, or sprayed onto the affected area using pump-type or aerosol sprayers.

Topical administration refers in this context to dermal or mucosal administration to the skin or mucous membrane.

The person of ordinary skill in the art will be well able to select suitable excipients in view of the selected formulation and form of administration, referring to e.g. handbooks such as Remington: The Science and Practice of Pharmacy 21st Edition. Philadelphia, Pa. Lippincott Williams & Wilkins. 2005.

In embodiments where a glucocorticoid is included in the pharmaceutical composition of the invention, care must be taken to define the optimal dose of the respective components, due to the herpes virus-stimulating effects of glucocorticoids. Too high a dose of the glucocorticoid might stimulate virus multiplication to an extent that can not be inhibited by the antiviral agent. With too low a dose the desired reduction of the symptoms of inflammation might not be achieved.

A pharmaceutical composition according to the present invention should contain a therapeutically effective amount of B-220. For example, the relative amount of B-220 in a pharmaceutical composition according to the present invention can be within the range of 0.1-10% (w/w), preferably 0.5-5% (w/w), e.g. about 1% (w/w).

In embodiments where an additional therapeutically active ingredient, such as any of the above-mentioned agents, is present in the composition, its concentration can be e.g. within the range of 0.005-5% (w/w), or within the range of 0.01-2% (w/w) or 0.25-1% (w/w).

In still another aspect, the present invention refers to a method of prophylactic and/or curative treatment of herpes virus infections of the skin or mucous membranes in a mammal subject, e.g. a human, comprising topical administration, in combination or in sequence, of a therapeutically effective dose of B-220 or a pharmaceutically acceptable salt thereof, and at least one additional pharmaceutically active ingredient as mentioned herein above.

EXAMPLE

B-220 (1 part) was mixed with white petrolatum (99 parts) in a homogenizer to provide a preparation in the form of an ointment, free of other components. This ointment is stable for more than 24 months and accordingly no stabilizers or conditioners had to be added. Variants of this preparation, e.g. containing a higher percentage of B-220, such as 2.5% (w/w) may be prepared in the same way.

Biological Tests

An ointment containing 1% by weight B-220 in white petrolatum was administered topically to 10 volunteers suffering from recurrent herpes labialis. The administration was performed repeatedly every day by applying a thin layer of the ointment to affected areas. All test subjects reported that pain surprisingly disappeared or was substantially alleviated within 1-2 days and redness disappeared or were substantially reduced within 2-4 days.

The invention claimed is:

1. A method of preventing and/or treating a herpes virus infection of the skin or mucous membranes in a mammal subject, comprising administering to the skin or mucous membranes of the subject an effective amount of a pharmaceutical composition comprising 2,3-dimethyl-6-(N,N-dimethylaminoethyl)-6H-indolo-[2,3-b]quinoxaline, or a pharmaceutically acceptable salt thereof, in a pharmaceutically acceptable carrier.

2. The method according to claim 1, wherein the pharmaceutical composition is administered topically.

3. The method according to claim 2, further comprising administering to the skin or mucous membranes of the subject an additional pharmaceutically active ingredient, in sequence or in combination with said pharmaceutical composition.

4. The method according to claim 3, wherein the additional pharmaceutically active ingredient is selected from antiviral agents, antibiotics, analgesics, anaesthetic agents, antiphlogistic agents and anti-inflammatory agents.

5. The method according to claim 3, wherein the pharmaceutical composition comprises the additional pharmaceutically active ingredient.

6. The method according to claim 2, wherein the pharmaceutical composition is in the form of a cream, liquid, lotion, gel, spray, foam or ointment.

7. The method according to claim 1, wherein the pharmaceutical composition comprises 2,3-dimethyl-6-(N,N-dimethylaminoethyl)-6H-indolo-[2,3-b]quinoxaline in an amount of 0.1-10% (w/w).

8. The method according to claim 1, wherein the pharmaceutical composition comprises 2,3-dimethyl-6-(N,N-dimethylaminoethyl)-6H-indolo-[2,3-b]quinoxaline in an amount of 0.5-5% (w/w).

9. The method according to claim 1, wherein the pharmaceutically acceptable carrier is white petrolatum.

* * * * *